(12) United States Patent
Vermerris et al.

(10) Patent No.: US 8,921,648 B2
(45) Date of Patent: *Dec. 30, 2014

(54) METHODS FOR INCREASING THE YIELD OF FERMENTABLE SUGARS FROM PLANT STOVER

(75) Inventors: Willem Evert Vermerris, Gainesville, FL (US); Michael R. Ladisch, Lafayette, IN (US); Nathan S. Mosier, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 712 days.

This patent is subject to a terminal disclaimer.

(21) Appl. No.: 13/158,558

(22) Filed: Jun. 13, 2011

(65) Prior Publication Data

US 2012/0058524 A1    Mar. 8, 2012

Related U.S. Application Data

(63) Continuation of application No. 11/416,006, filed on May 2, 2006, now Pat. No. 7,968,764.

(60) Provisional application No. 60/676,868, filed on May 2, 2005.

(51) Int. Cl.
| | | |
|---|---|---|
| C12N 15/63 | (2006.01) | |
| C12N 15/11 | (2006.01) | |
| C12N 15/52 | (2006.01) | |
| C12P 19/02 | (2006.01) | |
| C12P 7/10  | (2006.01) | |
| C13K 1/02  | (2006.01) | |

(52) U.S. Cl.
CPC .. *C12P 7/10* (2013.01); *Y02E 50/16* (2013.01); *C12P 19/02* (2013.01); *C13K 1/02* (2013.01)
USPC .......... 800/275; 800/278; 800/284; 800/286; 800/295; 435/320.1; 435/468; 536/23.1; 536/23.2; 536/23.6

(58) Field of Classification Search
None
See application file for complete search history.

(56) References Cited

U.S. PATENT DOCUMENTS

| | | | |
|---|---|---|---|
| 4,769,061 A | 9/1988 | Comai | |
| 4,810,648 A | 3/1989 | Stalker | |
| 4,940,835 A | 7/1990 | Shah et al. | |
| 4,975,374 A | 12/1990 | Goodman et al. | |
| 5,008,200 A | 4/1991 | Ranch et al. | |
| 5,015,580 A | 5/1991 | Christou et al. | |
| 5,024,944 A | 6/1991 | Collins et al. | |
| 5,266,317 A | 11/1993 | Tomalski et al. | |
| 5,322,783 A | 6/1994 | Tomes et al. | |
| 5,494,813 A | 2/1996 | Hepher et al. | |
| 5,563,055 A | 10/1996 | Townsend et al. | |
| 5,767,080 A * | 6/1998 | Beck et al. | 514/5.5 |
| 5,767,373 A | 6/1998 | Ward et al. | |
| 5,959,185 A | 9/1999 | Streit et al. | |
| 5,973,234 A | 10/1999 | Mueller et al. | |
| 5,977,445 A | 11/1999 | Soper et al. | |
| 6,063,947 A | 5/2000 | DeBonte et al. | |
| 6,282,837 B1 | 9/2001 | Ward et al. | |
| 6,288,306 B1 | 9/2001 | Ward et al. | |
| 6,323,392 B1 | 11/2001 | Charne | |
| 6,818,803 B1 | 11/2004 | Austin-Phillips et al. | |
| 7,968,764 B2 * | 6/2011 | Vermerris et al. | 800/275 |
| 2002/0138870 A1 * | 9/2002 | Chiang et al. | 800/278 |
| 2003/0109011 A1 * | 6/2003 | Hood et al. | 435/105 |
| 2003/0159170 A1 * | 8/2003 | Cahoon | 800/278 |

FOREIGN PATENT DOCUMENTS

| | | |
|---|---|---|
| EP | 0242246 A1 | 10/1987 |
| EP | 0333033 A1 | 9/1989 |
| WO | WO 92/13956 A1 | 8/1992 |
| WO | WO 92/13957 A1 | 8/1992 |
| WO | WO 93/02197 A1 | 2/1993 |
| WO | WO 93/11245 A1 | 6/1993 |
| WO | WO 93/19181 A1 | 9/1993 |
| WO | WO 94/00992 A1 | 1/1994 |
| WO | WO 95/16776 A1 | 6/1995 |
| WO | WO 95/18855 A2 | 7/1995 |
| WO | WO 96/30517 A1 | 10/1996 |
| WO | WO 96/30530 A1 | 10/1996 |
| WO | WO 99/07865 A1 | 2/1999 |
| WO | WO 01/12825 A1 | 2/2001 |
| WO | WO 01/29237 A2 | 4/2001 |
| WO | WO 02/14497 A2 | 2/2002 |
| WO | WO 2006/119318 A3 | 11/2006 |

OTHER PUBLICATIONS

Abe, K.; Emori, Y.; Kondo, H.; Suzuki, K.; Arai, S. "Molecular Cloning of a Cysteine Proteinase Inhibitor of Rice (Oryzacystatin)," *J. Biol. Chem.*, 1987, 262, 16793-16797.

Aono, M.; Saji, H.; Sakamoto, A.; Tanaka, K.; Kondo, N.; Tanaka, K. "Paraquat Tolerance of Transgenic *Nicotiana tabacum* With Enhanced Activities of Glutathione Reductase and Superoxide Dismutase," *Plant Cell Physiol.*, 1995, 36, 1687-1691.

Atanassova, R.; Chaubet, N.; Gigot, C. "A 126 bp Fragment of a Plant Histone Gene Promoter Confers Preferential Expression in Meristems of Transgenic *Arabidopsis*," *Plant J.*, 1992, 2, 291-300.

Barrière, Y.; Argillier, O. "Brown-Midrib Genes of Maize: A Review," *Agronomie*, 1993, 13, 865-876.

Barrière, Y.; Argillier, O.; Chabbert, B.; Tollier, M.T.; Monties, B. "Breeding Silage Maize With Brown-Midrib Genes. Feeding Value and Biochemical Characteristics," *Agronomie*, 1994, 14, 15-25.

(Continued)

*Primary Examiner* — Brent T Page
(74) *Attorney, Agent, or Firm* — Brinks Gilson & Lione

(57) ABSTRACT

Methods for increasing yield of fermentable sugars from plant stover are provided. The methods include using plants homozygous for two brown midrib mutations, bm1 and bm3. The methods also include using plants homozygous for a mutation in a gene that results in reduced cinnamyl alcohol dehydrogenase activity, and a mutation in a gene that results in reduced 5-hydroxyconiferaldehyde/5-hydroxyconiferyl alcohol O-methyltransferase activity. The methods also include using transgenic plants that have reduced cinnamyl alcohol dehydrogenase activity and reduced 5-hydroxyconiferaldehyde/5-hydroxyconiferyl alcohol O-methyltransferase activity in comparison with wild-type plants.

21 Claims, 7 Drawing Sheets

(56) References Cited

OTHER PUBLICATIONS

Beachy, R.N.; Loesch-Fries, S.; Turner, N.E. "Coat Protein-Mediated Resistance Against Virus Infection," *Ann. Rev. Phytopathol.*, 1990, 28, 451-474.

Becker, T.W.; Templeman, T.S.; Viret, J.F.; Bogorad, L. "The *cab*-m7 Gene: A Light-Inducible, Mesophyll-Specific Gene of Maize," *Plant Mol. Biol.*, 1992, 20, 49-60.

Botella, J.R.; Arteca, R.N. "Differential Expression of Two Calmodulin Genes in Response to Physical and Chemical Stimuli," *Plant Mol. Biol.*, 1994, 24, 757-766.

Briggs, S.P. "Grand Unification Theory in Sight," *Current Biology*, 1995, 5, 128-131.

Brown, L.; Torget, R. "Enzymatic Saccharification of Lignocellulosic Biomass," *Chemical Analysis and Testing Task Laboratory Analytical Procedure*, 1996, LAP-009, 9 pgs.

Bushnell, W.R.; Somers, D.A.; Giroux, R.W.; Szabo, L.J.; Zeyen, R.J. "Genetic Engineering of Disease Resistance in Cereals," *Can. J. Plant Path.*, 1998, 20, 137-149.

Chabannes, M.; Barakate, A.; Lapierre, C.; Marita, J.M.; Ralph, J.; Pean, M.; Danoun, S.; Halpin, C.; Grima-Pettenati, J.; Boudet, A.M. "Strong Decrease in Lignin Content Without Significant Alteration of Plant Development is Induced by Simultaneous Down-Regulation of Cinnamoyl CoA Reductase (CCR) and Cinnamyl Alcohol Dehydrogenase (CAD) in Tobacco Plants," *The Plant Journal*, 2001, 28, 257-270.

Chabbert, B.; Tollier, M.T.; Monties, B. "Biological Variability in Lignification of Maize: Expression of the Brown Midrib bm3 Mutation in Three Maize Cultivars," *J. Sci. Food Agric.*, 1994, 64, 349-355.

Chalfie, M.; Tu, Y.; Euskirchen, G.; Ward, W.W.; Prasher, D.C. "Green Fluorescent Protein as a Marker for Gene Expression," *Science*, 1994, 263, 802-805.

Charest, P.J.; Hattori, J.; DeMoor, J.; Iyer, V.N.; Miki, B.L. "In Vitro Study of Transgenic Tobacco Expressing *Arabidopsis* Wild Type and Mutant Acetohydroxyacid Synthase Genes," *Plant Cell Rep.*, 1990, 8, 643-646.

Cherney, D.J.R.; Cherney, J.H.; Patterson, J.A.; Axtell, J.D. "In Vitro Ruminal Fiber Digestion as Influenced by Phenolic-Carbohydrate Complexes Released From Sorghum Cell Walls," *Animal Feed Sci. Tech.*, 1992, 39, 79-93.

Cherney, J.H.; Cherney, D.J.R.; Akin, D.E.; Axtell, J.D. "Potential of Brown-Midrib, Low-Lignin Mutants for Improving Forage Quality," *Adv. Agron*, 1991, 46, 157-198.

Cherney, J.H.; Moore, K.J.; Volenec, J.J.; Axtell, J.D. "Rate and Extent of Digestion of Cell Wall Components of Brown-Midrib Sorghum Species," *Crop Science*, 1986, 26, 1055-1059.

Christensen, A.H.; Quail, P.H. "Sequence Analysis and Transcriptional Regulation by Heat Shock of Polyubiquitin Transcripts From Maize," *Plant Mol. Biol.*, 1989, 12, 619-632.

Christensen, A.H.; Sharrock, R.A.; Quail, P.H. "Maize Polyubiquitin Genes: Structure, Thermal Perturbation of Expression and Transcript Splicing, and Promoter Activity Following Transfer to Protoplasts by Electroporation," *Plant Mol. Biol.*, 1992, 18, 675-689.

Christou, P.; Murphy, J.E.; Swain, W.F. "Stable Transformation of Soybean by Electroporation and Root Formation From Transformed Callus," *Proc. Natl. Acad. Sci. USA*, 1987, 84, 3962-3966.

Close, P.S. "Cloning and Molecular Characterization of Two Nuclear Genes for *Zea mays* Mitochndrial Chaperonin 60," *Master's Thesis*, Iowa State University, 1993, 223 pages.

Comai, L.; Facciotti; D.; Hiatt, W.R.; Thompson, G.; Rose, R.E.; Stalker, D.M. "Expression in Plants of a Mutant *aroA* Gene from *Salmonella typhimurium* Confers Tolerance to Glyphosate," *Nature*, 1985, 317, 741-744.

Cornelissen, B.J.C.; Melchers, L.S. "Strategies for Control of Fungal Diseases with Transgenic Plants," *Plant Physiol.*, 1993, 101, 709-712.

Cox, W.J.; Cherney, D.J.R. "Influence of Brown Midrib, Leafy, and Transgenic Hybrids on Corn Forage Production," *Agron. J.*, 2001, 93, 790-796.

Creissen, G.; Edwards, E.A.; Enard, C.; Welburn, A.; Mullineaux P. "Molecular Characterization of Glutathione Reductase cDNAs from Pea (*Pisum sativum* L.)," *Plant J.*, 1991, 2, 129-131.

Datta, S.K.; Datta, K.; Soltanifar, N.; Donn, G.; Potrykus, I. "Herbicide-Resistant Indica Rice Plants From IRRI Breeding Line IR72 After PEG-Mediated Transformation of Protoplasts," *Plant Mol. Biol.*, 1992, 20, 619-629.

De Block, M.; Herrera-Estrella, L.; Van Montagu, M.; Schell, J.; Zambryski, P. "Expression of Foreign Genes in Regenerated Plants and in Their Projeny," *EMBO J.*, 1984, 3, 1681-1689.

De Greef, W.; Delon, R.; De Block, M.; Leemans, J.; Botterman, J. "Evaluation of Herbicide Resistance in Transgenic Crops Under Field Conditions," *Bio/Technology*, 1989, 7, 61-64.

Deshayes, A.; Herrera-Estrella, L.; Caboche, M. "Liposome-Mediated Transformation of Tobacco Mesophyll Protoplasts by an *Escherichia coli* Plasmid," *EMBO J.*, 1985, 4, 2731-2737.

D'Halluin, K.; Bonne, E.; Bossut, M.; De Beuckeleer, M.; Leemans, J. "Transgenic Maize Plants by Tissue Electroporation," *Plant Cell*, 1992, 4, 1495-1505.

Dhir, S.K.; Dhir, S.; Widholm, J.M. "Regeneration of Fertile Plants from Protoplasts of Soybean (*Glycine max* L. Merr.): Genotypic Differences in Culture Response," *Plant Cell Rep.*, 1992, 11, 285-289.

Draper, J.; Davey, M.R.; Freeman, J.P.; Cocking, E.C.; Cox, B.J. "Ti Plasmid Homologous Sequences Present in Tissues from *Agrobacterium* Plasmid-Transformed *Petunia* Protoplasts," *Plant Cell Physiol.*, 1982, 23, 451-458.

Eichholtz, D.A.; Rogers, S.G.; Horsch, R.B.; Klee, H.J.; Hayford, M.; Hoffmann, N.L.; Braford, S.B.; Fink, C.; Flick, J.; O'Connell, K.M.; Fraley, R.T. "Expression of Mouse Dihydrofolate Reductase Gene Confers Methotrexate Resistance in Transgenic Petunia Plants," *Somatic Cell Mol. Genet.*, 1987, 13, 67-76.

Elliott, K.J.; Butler, W.O.; Dickinson, C.D.; Konno, Y.; Vedvick, T.S.; Fitzmaurice, L.; Mirkov, T.E. "Isolation and Characterization of Fruit Vacuolar Invertase Genes From Two Tomato Species and Temporal Differences in mRNA Levels During Fruit Ripening," *Plant Mol. Biol.*, 1993, 21, 515-524.

Emerson, R.A.; Beadle, G.W.; Fraser, A.C. "A Summary of Linkage Studies in Maize," *Cornell Univ. Agric. Exp. Stn., Memoir 180*, 1935, 1-83.

Eyster W.H. "Chromosome VIII in Maize," *Science*, 1926, 64, 22.

Fisher, D.K.; Boyer, C.D.; Hannah, L.C. "Starch Branching Enzyme II From Maize Endosperm," *Plant Physiol.*, 1993, 102, 1045-1046.

Fraley, R.T.; Rogers, S.G.; Horsch, R.B.; Sanders, P.R.; Flick, J.S.; Adams, S.P.; Bittner, M.L.; Brand, L.A.; Fink, C.L.; Fry, J.S.; Galluppi, G.R.; Goldberg, S.B.; Hoffmann, N.L.; Woo, S.C. "Expression of Bacterial Genes in Plant Cells," *Proc. Natl. Acad. Sci. USA*, 1983, 80, 4803-4807.

Fontes E.B.P.; Shank, B.B.; Wrobel, R.L.; Moose, S.P.; OBrian, G.R.; Wurtzel, E.T.; Boston, R.S. "Characterization of an Immunoglobulin Binding Protein Homolog in the Maize *floury-2* Endosperm Mutant," *Plant Cell*, 1991, 3, 483-496.

Gatz, C.; Kaiser, A.; Wendenburg, R. "Regulation of a Modified CaMV 35S Promoter by the Tn*10*-encoded Tet Repressor in Transgenic Tobacco," *Mol. Gen. Genet.*, 1991, 227, 229-237.

Geiser, M.; Schweitzer, S.; Grimm, C. "The Hypervariable Region in the Genes Coding for Entomopathogenic Crystal Proteins of *Bacillus thuringiensis*: Nucleotide Sequence of the *kurhd1* Gene of Subsp. *kurstaki* HD1," Gene, 1986, 48, 109-118.

Gorden-Kamm, W.J.; Spencer, T.M.; Mangano, M.L.; Adams, T.R.; Daines, R.J.; Start, W.G.; O'Brien, J.V.; Chambers, S.A.; Adams, Jr., W.R.; Willetts, N.G.; Rice, T.B.; Mackey, C.J.; Krueger, R.W.; Kausch, A.P.; Lemaux, P.G. "Transformation of Maize Cells and Regeneration of Fertile Transgenic Plants," *Plant Cell*, 1990, 2, 603-618.

Goto, M.; Matsuoka, J.; Sato, T.; Ehara, H.; Morita, O. "Brown Midrib Mutant Maize With Reduced Levels of Phenolic Acids Ether-Linked to the Cell Walls," *Anim. Feed Sci. Technol.*, 1994, 48, 27-38.

Gould, S.J.; Keller, G-A.; Hosken, N.; Wilkinson, J.; Subramani, S. "A Conserved Tripeptide Sorts Proteins to Peroxisomes," *J. Cell. Biol.*, 1989, 108, 1657-1664.

(56) References Cited

OTHER PUBLICATIONS

Grabber, J.H.; Ralph, J.; Hatfield, R.D. "Severe Inhibition of Maize Wall Degradation by Synthetic Lignins Formed with Coniferaldehyde," *J. Sci. Food Agric.*, 1998, 78, 81-87.
Grabber, J.H.; Ralph, J.; Hatfield, R.D.; Quideau, S. "*p*-Hydroxyphenyl, Guaiacyl, and Syringyl Lignins Have Similar Inhibitory Effects on Wall Degradability," *J. Agric. Food Chem.*, 1997, 45, 2530-2532.
Griess, E.A.; Igloi, G.L.; Feix, G. "Isolation and Sequence Comparison of a Maize Calmodulin cDNA," *Plant Physiol.*, 1994, 104, 1467-1468.
Gruber, M.Y.; Crosby, W.L. "Chapter 7—Vectors for Plant Transformation," *Methods in Plant Molecular Biology and Biotechnology*, Glick, B.R.; Thompson, J.E. (eds), CRC Press, Inc., 1993, Boca Raton, 89-119.
Guerrero, F.D.; Crossland, L.; Smutzer, G.S.; Hamilton, D.A.; Mascarenhas, J.P. "Promoter Sequences From a Maize Pollen-Specific Gene Direct Tissue-Specific Transcription in Tobacco," *Mol. Gen. Genet.*, 1990, 224, 161-168.
Hain, R.; Stabel, P.; Czernilofsky, A.P.; Steinbilβ, H.H.; Herrera-Estrella, L.; Schell, J. "Uptake, Integration, Expression and Genetic Transmission of a Selectable Chimaeric Gene by Plant Protoplasts," *Mol. Gen. Genet.*, 1985, 199, 161-168.
Hallauer, A.R. "Chapter 8—Maize," *Principles of Cultivar Development*, Fehr; W. (ed.), Macmillan Publishing Company, 1987, New York, 249-294.
Halpin, C.; Holt, K.; Chojecki, J.; Oliver, D.; Chabbert, B.; Monties, B.; Edwards, K.; Barakate, A.; Foxon, G.A. "*Brown-midrib* Maize (bm1)—a Mutation Affecting the Cinnamyl Alcohol Dehydrogenase Gene," *Plant J.*, 1998, 14, 545-553.
Hammock, B.D.; Bonning, B.C.; Possee, R.D.; Hanzlik, T.N.; Maeda, S. "Expression and Effects of the Juvenile Hormone Esterase in a Baculovirus Vector," *Nature*, 1990, 344, 458-461.
Hartley, R.D.; Jones, E.C. "Phenolic Components and Degradability of the Cell Walls of the Brown Midrib Mutant, $bm_3$, of *Zea mays*," *J. Sci. Fd. Agric.*, 1978, 29, 777-789.
Hattori, J.; Brown, D.; Mourad, G.; Labbé, H.; Ouellet, T.; Sunohara, G.; Rutledge, R.; King, J.; Miki, B. "An Acetohydroxy Acid Synthase Mutant Reveals a Single Site Involved in Multiple Herbicide Resistance," *Mol. Gen. Genet.*, 1995, 246, 419-425.
Hayes, J.D.; Judah, D.J.; Neal, G.E.; Nguyen, T. "Molecular Cloning and Heterologous Expression of a cDNA Encoding a Mouse Glutathione *S*-transferase Yc Subunit Possessing High Catalytic Activity for Aflatoxin $B_1$-8,9-epoxide," *Biochem. J.*, 1992, 285, 173-180.
Hayford, M.B.; Medford, J.I.; Hoffman, N.L.; Rogers, S.G.; Klee, H.J. "Development of a Plant Transformation Selection System Based on Expression of Genes Encoding Gentamicin Acetyltransferases," *Plant Physiol.*, 1988, 86, 1216-1222.
Heney, G.; Orr, G.A. "The Purification of Avidin and Its Derivatives on 2-Iminobiotin-6-aminohexyl-Sepharose 4B," *Anal. Biochem.*, 1981, 114, 92-96.
Higuchi, T.; Ito, T.; Umezawa, T.; Hibino, T.; Shibata, D. "Red-Brown Color of Lignified Tissues of Transgenic Plants With Antisense CAD Gene: Wine-Red Lignin From Coniferyl Aldehyde," *J. Biotechnol.*, 1994, 37, 151-158.
Hille, J.; Verheggen, F.; Roelvink, P.; Franssen, H.; van Kammen, A.; Zabel, P. "Bleomycin Resistance: A New Dominant Selectable Marker for Plant Cell Transformation," *Plant Mol. Biol.*, 1986, 7, 171-176.
Horsch, R.B.; Fry, J.E.; Hoffmann, N.L.; Eichholtz, D.; Rogers, S.G.; Fraley, R.T. "A simple and General Method for Trasferring Genes into Plants," *Science*, 1985, 227, 1229-1231.
Humphreys, J.M.; Hemm, M.R.; Chapple, C. "New Routes for Lignin Biosynthesis Defined by Biochemical Characterization of Recombinant Ferulate 5-hydroxylase, a Multifunctional Cytochrome P450-Dependent Monooxygenase," *Proc. Natl. Acad. Sci. USA*, 1999, 96, 10045-10050.

"ImaGene Green™ $C_{12}$FDGlcU GUS Gene Expression Kit (I-2908)," Product Information Sheet, *Molecular Probes Publication 02908*, 1997, 1-4.
Jaynes, J.M.; Nagpala, P.; Destéfano-Beltrán, L; Huang, J.H.; Kim, JH; Denny, T.; Cetiner, S. "Expression of a Cecropin B Lytic Peptide Analog in Transgenic Tobacco Confers Enhanced Resistance to Bacterial Wilt Caused by *Pseudomonas Solanacearum*," *Plant Sci.*, 1993, 89, 43-53.
Jefferson, R.A. "Experimental Protocols—Assaying Chimeric Genes in Plants: The GUS Gene Fusion System," *Plant Mol. Biol. Rep.*, 1987, 5, 387-405.
Jones, D.A.; Thomas, C.M.; Hammond-Kosack, K.E.; Balint-Kurti, P.J.; Jones, J.D.G. "Isolation of the Tomato Cf-9 Gene for Resistance to *Cladosporium fulvum* by Transposon Tagging," *Science*, 1994, 266, 789-793.
Jones, J.D.G.; Svab, Z.; Harper, E.C.; Hurwitz, C.D.; Maliga, P. "A Dominant Nuclear Streptomycin Resistance Marker for Plant Cell Transformation," *Mol. Gen. Genet.*, 1987, 210, 86-91.
Kado, C.I. "Molecular Mechanisms of Crown Gall Tumorigenesis," *Crit. Rev. Plant Sci.*, 1991, 10, 1-32.
Kalderon, D.; Roberts, B.L.; Richardson, W.D.; Smith, A.E. "A Short Amino Acid Sequence Able to Specify Nuclear Location," *Cell*, 1984, 39, 499-509.
Kawalleck, P.; Somssich, I.E.; Feldbrugge, M.; Hahlbrock, K.; Weisshaar, B. "Polyubiquitin Gene Expression and Structural Properities of the *ubi4-2* Gene in *Petroselinum crispum*," *Plant Mol. Biol.*, 1993, 21, 673-684.
Klein, T.M.; Arentzen, R.; Lewis, P.A.; Fitzpatrick-McElligott, S. "Transformation of Microbes, Plants and Animals by Particle Bombardment," *Bio/Technology*, 1992, 10, 286-291.
Klein, T.M.; Gradziel, T.; Fromm, M.E.; Sanford, J.C. "Factors Influencing Gene Delivery into *Zea Mays* Cells by High-Velocity Microprojectiles," *Bio/Technology*, 1988, 6, 559-563.
Komatsuda, T.; Kaneko, K.; Oka, S. "Cell Biology & Molecular Genetics," *Crop Sci.*, 1991, 31, 333-337.
Komatsuda, T.; Lee, W.; Oka, S. "Maturation and Germination of Somatic Embryos as Affected by Sucrose and Plant Growth Regulators in Soybeans *Glycine gracilis* Skvortz and *Glycine max* (L.) Merr.," *Plant Cell, Tissue and Organ Culture*, 1992, 28, 103-113.
Koncz, C.; Olsson, O.; Langridge, W.H.R.; Schell, J.; Szalay, A.A. "Expression and Assembly of Functional Bacterial Luciferase in Plants," *Proc. Natl. Acad. Sci. USA*, 1987, 84, 131-135.
Knox, C.A.P.; Sonthayanon, B.; Chandra, G.R.; Muthukrishnan, S. "Structure and Organization of Two Divergent α-amylase Genes From Barley," *Plant Mol. Biol.*, 1987, 9, 3-17.
Knutzon, D.S.; Thompson, G.A.; Radke, S.E.; Johnson, W.B.; Knauf, V.C.; Kridl, J.C. "Modification of Brassica Seed Oil by Antisense Expression of a Stearoyl-acyl Carrier Protein Desaturase Gene," *Proc. Natl. Acad. Sci. USA*, 1992, 89, 2624-2628.
Kramer, K.J.; Corpuz, L.; Choi, H.K.; Muthukrishnan, S. "Sequence of a cDNA and Expression of the Gene Encoding Epidermal and Gut Chitinases of *Manduca sexta*," *Insect Biochem. Molec. Biol.*, 1993, 23, 691-701.
Kuc, J.; Nelson, O.E. "The Abnormal Lignins Produced by the *Brown-Midrib* Mutants of Maize," *Arch. Biochem. Biophys*, 1964, 105, 103-113.
Lamb, C.J.; Ryals, J.A.; Ward, E.R.; Dixon, R.A. "Review/Emerging Strategies for Enhancing Crop Resistance to Microbial Pathogens," *Bio/Technology*, 1992, 10, 1436-1445.
Landry B.S. "Chapter 17—DNA Mapping in Plants," *Methods in Plant Molecular Biology and Biotechnology*, Glick, B.R.; Thompson, J.E. (eds), CRC Press, Inc., 1993, Boca Raton, 269-285.
Last, D.I.; Brettell, R.I.S.; Chamberlain, D.A.; Chaudhury, A.M.; Larkin, P.J.; Marsh, E.L.; Peacock, W.J.; Dennis, E.S. "pEmu: An Improved Promoter for Gene Expression in Cereal Cells," *Theor. Appl. Genet.*, 1991, 81, 581-588.
Lauer, J. "Corn Silage Yield and Quality Trade-Offs When Changing Cutting Height," *Agronomy Advice.*, 2010, http://com.agronomy.wisc.edu, 2 pages.
Lauer, J.; Coors, J. "Brown Midrib Corn," *Agronomy Advice.*, 2010, http://corn.agronomy.wisc.edu, 3 pages.

(56) References Cited

OTHER PUBLICATIONS

Laursen, C.M.; Krzyzek, R.A.; Flick, C.E.; Anderson, P.C.; Spencer, T.M. "Production of Fertile Transgenic Maize by Electroporation of Suspension Culture Cells," *Plant Mol. Biol.*, 1994, 24, 51-61.
Lechtenberg, V.L.; Muller, L.D.; Bauman, L.F.; Rhykerd, C.L.; Barnes, R.F. "Laboratory and In Vitro Evaluation of Inbred and F$_2$ Populations of Brown Midrib Mutants of *Zea mays* L.," *Agronomy J.*, 1972, 64, 657-660.
Lee, K.Y.; Townsend, J.; Tepperman, J.; Black, M.; Chui, C.F.; Mazur, B.; Dunsmuir, P.; Bedbrook, J. "The Molecular Basis of Sulfonylurea Herbicide Resistance in Tobacco," *EMBO J.*, 1988, 7, 1241-1248.
Lee, M.H.; Brewbaker, J.L. "Effects of Brown Midrib-3 on Yields and Yield Components of Maize," *Crop. Sci.*, 1984; 24:105-108, (Abstract only) http://crop.scijournals.org/cgi/content/abstract/24/1/105, 1 page.
Lepetit, M.; Ehling, M.; Chaubet, N.; Gigot, C. "A Plant Histone Gene Promoter Can Direct Both Replication-Dependent and -independent Gene Expression in Transgenic Plants," *Mol. Gen. Genet.*, 1992, 231, 276-285.
Lerner, D.R.; Raikhel, N.V. "Cloning and Characterization of Root-Specific Barley Lectin," *Plant Physiol.*, 1989, 91, 124-129.
Li, L.; Popko, J.L.; Umezawa, T.; Chiang, V.L. "5-Hydroxyconiferyl Aldehyde Modulates Enzymatic Methylation for Syringyl Monolignol Formation, a New View of Monolignol Biosynthesis in Angiosperms," *The Journal of Biological Chemistry*, 2000, 275, 6537-6545.
Linthorst, H.J.M.; Brederode, F.T.; van der Does, C.; Bol, J.F. "Tobacco Proteinase, Inhibitor I Genes are Locally, But Not Systemically Induced by Stress," *Plant Mol. Biol.*, 1993, 21, 985-992.
Logemann, J.; Jach, G.; Tommerup, H.; Mundy, J.; Schell, J. "Expression of a Barley Ribosome-Inactivating Protein Leads to Increased Fungal Protection in Transgenic Tobacco Plants," *Bio/Technology*, 1992, 10, 305-308.
Marshall, L.C.; Somers, D.A.; Dotray, P.D.; Gengenbach, B.G.; Wyse, D.L.; Gronwald, J.W. "Allelic Mutations in Acetyl-Coenzyme A Carboxylase Confer Herbicide Tolerance in Maize," *Theor. Appl. Genet.*, 1992, 83, 435-442.
Martin, G.B.; Brommonschenkel, S.H.; Chunwongse, J.; Frary, A.; Ganal, M.W.; Spivey, R.; Wu, T.; Earle, E.D.; Tanksley, S.D. "Map-Based Cloning of a Protein Kinase Gene Conferring Disease Resistance in Tomato," *Science*, 1993, 262, 1432-1436.
Matsuoka, K.; Nakamura, K. "Propeptide of a Precursor to a Plant Vacuolar Protein Required for Vacuolar Targeting," *Proc. Natl. Acad. Sci. USA*, 1991, 88, 834-838.
McElroy, D.; Zhang, W.; Cao, J.; Wu, R. "Isolation of an Efficient Actin Promoter for Use in Rice Transformation," *Plant Cell*, 1990, 2, 163-171.
Mett, V.L.; Lochhead, L.P.; Reynolds, P.H.S. "Copper-Controllable Gene Expression System for Whole Plants," *Proc. Natl. Acad. Sci. USA*, 1993, 90, 4567-4571.
Miki, B.L.; Fobert, P.F.; Charest, P.J.; Iyer, V.N. "Chapter 6—Procedures for Introducing Foreign DNA into Plants," *Methods in Plant Molecular Biology and Biotechnology*, Glick, B.R.; Thompson, J.E. (eds), CRC Press, Inc., 1993, Boca Raton, 67-88.
Miki, B.L.; Labbé, H.; Hattori, J.; Ouellet, T.; Gabard, J.; Sunohara, G.; Charest, P.J.; Iyer, V.N. "Transformation of *Brassica napus* Canola Cultivars with *Arabidopsis thaliana* Acetohydroxyacid Synthase Genes and Analysis of Herbicide Resistance," *Theor. Appl. Genet.*, 1990, 80, 449-458.
Mindrinos, M.; Katagiri, F.; Yu, G-L.; Ausubel, F.M. "The *A. thaliana* Disease Resistance Gene *RPS2* Encodes a Protein Containing a Nucleotide-Binding Site and Leucine-Rich Repeats," *Cell*, 1994, 78, 1089-1099.
Moloney, M.M.; Walker, J.M.; Sharma, K.K. "High Efficiency Transformation of *Brassica napus* Using *Agrobacterium* Vectors," *Plant Cell Rep.*, 1989, 8, 238-242.
Morreel, K.; Ralph, J.; Lu, F.; Goeminne, G.; Busson, R.; Herdewijn, P.; Goeman, J.L.; Van der Eycken, J.; Boerjan, W.; Messens, E. "Phenolic Profiling of Caffeic Acid *O*-Methyltransferase-Deficient Poplar Reveals Novel Benzodioxane Oligolignols," *Plant Physiology*, 2004, 136, 4023-4036.
Morrison, F.B.; Humphrey, G.C.; Hulce, R.S. "Corn Stover Silage Versus Corn Silage for Milk Production," *J. Anim. Sci.*, 1921, 58-59 (3 pages).
Morrison, T.A.; Kessler, J.R.; Hatfield, R.D.; Buxton, D.R. "Activity of Two Lignin Biosynthesis Enzymes During Development of a Maize Internode," *J. Sci. Food Acric.*, 1994, 65, 133-139.
Mueller, J.P.; Green, J.T.; Kjelgaard, W.L. "Corn Silage Harvest Techniques," *National Corn Handbook*, Iowa State University, 1991, NCH-49, 7 pages.
Muller, L.D.; Barnes, R.F.; Bauman, L.F.; Colenbrander, V.F. "Variations in Lignin and Other Structural Components of Brown Midrib Mutants of Maize," *Crop Science*, 1971, 11, 413-415.
Murai, N.; Sutton, D.W.; Murray, M.G.; Slightom, J.L.; Merlo, D.J.; Reichert, N.A.; Sengupta-Gopalan, C.; Stock, C.A.; Barker, R.F.; Kemp, J.D.; Hall, T.C. "Phaseolin Gene from Bean is Expressed After Transfer to Sunflower Via Tumor-Inducing Plasmid Vectors," *Science*, 1983, 222, 476-482.
Naleway, J.J.; Zhang, Y.Z.; Bonnett, H.; Galbraith, D.W.; Haugland, R.P. "Detection of GUS Gene Expression in Transformed Plant Cells With New Lipophilic, Fluorogenic β-Glucuronidase Substrate," *J. Cell Biol.*, 1991, 115, 151a.
Odell, J.T.; Nagy, F.; Chua, N-H. "Identification of DNA Sequences Required for Activity of the Cauliflower Mosaic Virus 35S Promoter," *Nature*, 1985, 313, 810-812.
Ostrander, B.; Maillot, M.P.; Toillon, S.; Barrière, Y.; Pollacsek, M.; Besle, J.M. "Cell Wall Phenolics and Digestibility of Normal and Brown Midrib Maizes in Different Stem Sections and Across Maturity Stages," *J. Sci. Food Agric.*, 1999, 79, 414-415.
Pandey, P.; Bansal, Y.K. "Plant Regeneration from Leaf and Hypocotyl Explants of *Glycine wightii* (W. and A.) VERDC. var *logicauda*," *Japan J. Breed.*, 1992, 42, 1-5.
Pang, S-Z.; Oberhaus, S.M.; Rasmussen, J.L.; Knipple, D.C.; Bloomquist, J.R.; Dean, D.H.; Bowman, K.D.; Sanford, J.C. "Expression of a Gene Encoding a Scorpion Insectotoxin Peptide in Yeast, Bacteria and Plants," *Gene*, 1992, 116, 165-172.
Paul, W.; Hodge, R.; Smartt, S.; Draper, J.; Scott, R. "The Isolation and Characterisation of the Tapetum-Specific *Arabidopsis thaliana* A9 Gene," *Plant Mol. Biol.*, 1992, 19, 611-622.
Pedersen, J.F.; Vogel, K.P.; Funnell, D.L. "Impact of Reduced Lignin on Plant Fitness," *Crop Sci.*, 2005, 45, 812-819.
Pen, J.; Molendijk, L.; Quax, W.J.; Sijmons, P.C.; van Ooyen, A.J.J.; van den Elzen, P.J.M.; Rietveld, K.; Hoekema, A. "Production of Active *Bacillus Licheniformis* Alpha-Amylase in Tobacco and Its Application in Starch Liquefaction," *Bio/Technology*, 1992, 10, 292-296.
Pratt, G.E.; Farnsworth, D.E.; Siegel, N.R.; Fok, K.F.; Feyereisen, R. "Identification of an Allatostatin From Adult *Diploptera Punctata*," *Biochem. Biophys. Res. Comm.*, 1989, 163, 1243-1247.
Provan, G.J.; Scobbie, L.; Chesson, A. "Characterisation of Lignin from CAD and OMT Deficient *Bm* Mutants of Maize," *J. Sci. Food. Agric.*, 1997, 73, 133-142.
Przibilla, E.; Heiss, S.; Johanningmeier, U.; Trebst, A. "Site-Specific Mutagenesis of the D1 Subunit of Photosystem II in Wild-Type *Chlamydomonas*," *Plant Cell*, 1991, 3, 169-174.
Raboy, V.; Dickinson, D.B.; Neuffer, M.G. "A Survey of Maize Kernel Mutants for Variation in Phytic Acid," *Maydica*, 1990, 35, 383-390.
Regan, J.D. "Expression Cloning of an Insect Diuretic Hormone Receptor," *J. Biol. Chem.*, 1994, 269, 9-12.
Röder, F.T.; Schmülling, T.; Gatz, C. "Efficiency of the Tetracycline-Dependent Gene Expression System: Complete Suppression and Efficient Induction of the *rolB* Phenotype in Transgenic Plants," *Mol. Gen. Genet.*, 1994, 243, 32-38.
Saballos, A.; Ejeta, G.; Sanchez, E.; Kang, CH.; Vermerris, W. "A Genomewide Analysis of the Cinnamyl Alcohol Dehydrogenase Family in Sorghum [*Sorghum bicolor* (L.) Moench] Identifies *SbCAD2* as the *Brown midrib6* Gene," *Genetics*, 2009, 181, 783-795.
Sanford, J.C. "Biolistic Plant Transformation," *Physiol. Plant.*, 1990, 79, 206-209.

(56) References Cited

OTHER PUBLICATIONS

Sanford, J.C. "Reviews—The Biolistic Process," *TIBTECH*, 1988, 6, 299-302.

Sanford, J.C.; Klein, T.M.; Wolf, E.D.; Allen, N. "Delivery of Substances into Cells and Tissues Using a Particle Bombardment Process," *Part. Sci. Technol.*, 1987, 5, 27-37.

Schena, M.; Lloyd, A.M.; Davis, R.W. "A Steroid-Inducible Gene Expression System for Plant Cells," *Proc. Natl. Acad. Sci. USA*, 1991, 88, 10421-10425.

Sengupta-Gopalan, C.; Reichert, N.A.; Barker, R.F.; Hall, T.C.; Kemp, J.D. "Developmentally Regulated Expression of the Bean β-phaseolin Gene in Tobacco Seed," *Proc. Natl. Acad. Sci. USA*, 1985, 82, 3320-3324.

Shah, D.M.; Horsch, R.B.; Klee, H.J.; Kishore, G.M.; Winter, J.A.; Turner, N.E.; Hironaka, C.M.; Sanders, P.R.; Gasser, C.S.; Aykent, S.; Siegel, N.R.; Rogers, S.G.; Fraley, R.T. "Engeineering Herbicide Tolerance in Transgenic Plants," *Science*, 1986, 233, 478-481.

Shetty, K.; Asano, Y.; Oosawa K. "Stimulation of In Vitro Shoot Organogenesis in *Glycine max* (Merrill.) by Allantoin and Amides," *Plant Sci.*, 1992, 81, 245-251.

Shiota, N.; Nagasawa, A.; Sakaki, T.; Yabusaki, Y.; Ohkawa, H. "Herbicide-Resistant Tobacco Plants Expressing the Fused Enzyme Between Rat Cytochrome P4501A1 (CYP1A1) and Yeast NADPH—Cytochrome P450 Oxidoreductase," *Plant Physiol.*, 1994, 106, 17-23.

Shiroza, T.; Kuramitsu, H.K. "Sequence Analysis of the *Streptococcus mutans* Fructosyltransferase Gene and Flanking Regions," *J. Bacteriol.*, 1988, 170, 810-816.

Sibout, R.; Eudes, A.; Mouille, G.; Pollet, B.; Lapierre, C.; Jouanin, L.; Séguin, A. "Cinnamyl Alcohol Dehydrogenase-C and -D are the Primary Genes Involved in Lignin Biosynthesis in the Floral Stem of *Arabidopsis*," *The Plant Cell*, 2005, 17, 2059-2076.

Simpson, J.; Timko, M.P.; Cashmore, A.R.; Schell, J.; Van Montagu, M.; Herrera-Estrella, L. "Light-Induced and Tissue-Specific Expression of a Chimaeric Gene Under Control of the 5'-Flanking Sequence of a Pea Chlorophyll *a/b*—Binding Protein Gene," *EMBO J.*, 1985, 4, 2723-2729.

Søgaard, M.; Kadziola, A.; Haser, R.; Svensson, B. "Site-Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-Amylase 1," *J. Biol. Chem.*, 1993, 268, 22480-22484.

Stalker, D.M.; McBride, K.E.; Malyj, L.D. "Herbicide Resistance in Transgenic Plants Expressing a Bacterial Detoxification Gene," *Science*, 1988, 242, 419-423.

Steifel, V.; Ruiz-Avila, L.; Raz, R.; Vallés, M.P.; Gómez, J.; Pagés, M.; Martinez-Izquierdo, J.A.; Ludevid, M.D.; Langdale, J.A.; Nelson, T.; Puigdomènech, P. "Expression of a Maize Cell Wall Hydroxyproline-Rich Glycoprotein Gene in Early Leaf and Root Vascular Differentiation," *Plant Cell*, 1990, 2, 785-793.

Steinmetz, M.; Le Coq, D.; Aymerich, S.; Gonzy-Tréboul, G.; Gay, P. "The DNA Sequence of the Gene for the Secreted *Bacillus subtilis* Enzyme levansucrase and Its Genetic Control Sites," *Mol. Gen. Genet.*, 1985, 200, 220-228.

Stephens, P.A.; Nickell, C.D.; Widholm, J.M. "Agronomic Evaluation of Tissue-Culture-Derived Soybean Plants," *Theor, Appl. Genet.*, 1991, 82, 633-635.

Sumitani, J-i.; Kawaguchi, T.; Hattori, N.; Murao, S.; Arai, M. "Molecular Cloning and Expression of Proteinaceous α-Amylase Inhibitor Gene from *Streptomyces nitrosporeus* in *Escherichia coli*," *Biosci. Biotech. Biochem.*, 1993, 57, 1243-1248.

Svab, Z.; Harper, E.C.; Jones, J.D.G.; Maliga, P. "Aminoglycoside -3"—Adenyltransferase Confers Resistance to Spectinomycin and Streptomycin in *Nicotiana tabacum*, *Plant Mol. Biol.*, 1990, 14, 197-205.

Tavladoraki, P.; Benvenuto, E.; Trinca, S.; De Martinis, D.; Cattaneo, A.; Galeffi, P. "Transgenic Plants Expressing a Functional Single-Chain Fv Antibody are Specifically Protected From Virus Attack," *Nature*, 1993, 366, 469-472.

Teeri, T.H.; Lehväslaiho, H.; Franck, M.; Uotila, J.; Heino, P.; Palva, E.T.; Van Montagu, M.; Herrera-Estrella, L. "Gene Fusions to *lacZ* Reveal New Expression Patterns of Chimeric Genes in Transgenic Plants," *EMBO J.*, 1989, 8, 343-350.

Timko, M.P.; Kausch, A.P.; Castresana, C.; Fessler, J.; Herrera-Estrella, L.; Van den Broeck, G.; Van Montagu, M.; Schell, J.; Cashmore, A.R. "Light Regulation of Plant Gene Expression by an Upstream Enhancer-Like Element," *Nature*, 1985, 318, 579-582.

Tjardes, K.E.; Buskirk, D.D.; Allen, M.S.; Ames, N.K.; Bourquin, L.D.; Rust, S.R. "Brown Midrib-3 Corn Silage Improves Digestion But Not Performance of Growing Beef Steers," *J. Anim. Sci.*, 2000, 78, 2957-2965.

Toubart, P.; Desiderio, A.; Salvi, G.; Cervone, F.; Daroda, L.; De Lorenzo, G. "Cloning and Characterization of the Gene Encoding the Endopolygalacturonase—Inhibiting Protein (PGIP) of *Phaseolus vulgaris* L.," *Plant J.*, 1992, 2, 367-373.

Twell, D.; Wing, R.; Yamaguchi, J.; McCormick, S. "Isolation and Expression of an Anther-Specific Gene From Tomato," *Mol. Gen. Genet.*, 1989, 217, 240-245.

Twell, D.; Patel, S.; Sorensen, A.; Roberts M.; Scott, R.; Draper, J.; Foster, G. "Activation and Developmental Regulation of a *Arabidopsis* Anther-Specific Promoter in Microspores and Pollen of *Nicotiana Tabacum*," *Sex Plant Reprod.*, 1993, 6, 217-224.

Van Damme, E.J.M.; Smeets, K.; Van Leuven, F.; Peumans, W.J. "Molecular Cloning of Mannose-Binding Lectins from *Clivia miniata*," *Plant Mol. Biol.*, 1994, 24, 825-830.

van den Elzen, P.J.M.; Townsend, J.; Lee, K.Y.; Bedbrook, J.R. "A Chimaeric Hygromycin Resistance Gene as a Selectable Marker in Plant Cells," *Plant Mol. Biol.*, 1985, 5, 299-302.

van Hartingsveldt, W.; van Zeijl, C.M.J.; Harteveld, G.M.; Gouka, R.J.; Suykerbuyk, M.E.G.; Luiten, R.G.M.; van Paridon, P.A.; Selten, G.C.M.; Veenstra, A.E.; van Gorcom, R.F.M.; van den Hondel, C.A.M.J.J. "Cloning, Characterization and Overexpression of the Phytase-Encoding Gene (*phyA*) of *Aspergillus niger*," *Gene*, 1993, 127, 87-94.

Van Parijs, J.; Broekaert W.F.; Goldstein, I.J.; Peumans, W.J. "Hevein: An Antifungal Protein From Rubber-Tree (*Hevea brasiliensis*) Latex," *Planta*, 1991, 183, 258-264.

Varghabutler, E.I.; Sveinsson, S.J.; Policova, Z. "Wettability Studies on Drugs and Drug Delivery Vesicles," *Colloids and Surfaces*, 1991, 58, 271-286, (2 page abstract only).

Velten, J.; Velten, L.; Hain, R.; Schell, J. "Isolation of a Dual Plant Promoter Fragment From the Ti Plasmid of *Agrobacterium tumefaciens*," *Embo J.*, 1984, 3, 2723-2730.

Vermerris, W.; Ladisch, M.R.; Mosier, N.S. "Modifying Lignin Composition to Enhance Ethanol Production," CPBR Semiannual Progress Report, 2005, 1-10.

Vermerris, W.; McIntyre, L.M. "Time to Flowering in *brown midrib* Mutants of Maize: An Alternative Approach to the Analysis of Developmental Traits," *Heredity*, 1999, 83, 171-178.

Vermerris, W., Thompson, K.J.; McIntyre, L.M. "The Maize *Brown midrib1* Locus Affects Cell Wall Composition and Plant Development in a Dose-Dependent Manner," *Heredity*, 2002, 88, 450-457.

Vermerris, W.; Thompson, K. J.; McIntyre, L.M.; Axtell, J.D. "Evidence for an Evolutionarily Conserved Interaction Between Cell Wall Biosynthesis and Flowering in Maize and Sorghum," *BMC Evol. Bio.*, 2002, 2, 2 (8 pages).

Vignols, F.; Rigau, J.; Torres, M.A.; Capellades, M.; Puigdomenech, P. "The *brown midrib3* (*bm3*) Mutation in Maize Occurs in the Gene Encoding Caffeic Acid *O*-Methyltransferase," *Plant Cell*, 1995, 7, 407-416.

Ward, E.R.; Ryals, J.A.; Miflin, B.J. "Chemical Regulation of Transgene Expression in Plants," *Plant Mol. Biol.*, 1993, 22, 361-366.

Whetten, R.; Sederoff, R. "Lignin Biosynthesis," *The Plant Cell*, 1995, 7, 1001-1013.

Zhang, L-J.; Cheng, L-M.; Xu, N.; Zhao, N-M.; Li, C-G.; Yuan, J.; Jia, S-R. "Efficient Transformation of Tobacco by Ultrasonication," *Nature Biotechnology*, 1991, 9, 996-997.

\* cited by examiner

A

METHODS FOR INCREASING THE YIELD OF FERMENTABLE SUGARS FROM PLANT STOVER

This application is a continuation of U.S. application Ser. No. 11/416,006, filed May 2, 2006 now U.S. Pat. No. 7,687,764, which claims the benefit of U.S. provisional patent application Ser. No. 60/676,868, filed May 2, 2005, the entire contents of both of which are incorporated herein by reference in their entireties.

GOVERNMENT INTERESTS

The development of the present invention was supported by DOE project funds. The U.S. Government may have certain rights in the invention described herein.

TECHNICAL FIELD

The present invention relates to methods for increasing the yield of fermentable sugars in a plant stover.

BACKGROUND

Unlike other renewable energy sources, biomass can be converted directly into liquid fuels. The two most common types of biofuels are ethanol (ethyl alcohol) and biodiesel. Ethanol is an alcohol, which can be produced by fermenting any biomass high in carbohydrates (starches, sugars, or celluloses) through a process similar to brewing beer, once fermentable sugars have been obtained from the biomass material. The breakdown of the biomass into monomers (monosaccharides) requires the material to be softened through pretreatment, enzymes be added that hydrolyze the polymeric forms of sugars contained in the biomass into monosaccharides, and fermentation of both the 6-carbon and 5-carbon sugars to ethanol or to other desired bio-products.

Ethanol production in the United States grew from just a few million gallons in the mid-1970s to over 3.9 billion gallons in 2005. National energy security concerns, new Federal gasoline standards, and Government incentives have been the primary stimuli for this growth. Ethanol is mostly used as a fuel additive to cut down a vehicle's carbon monoxide and other smog-causing emissions. Flexible-fuel vehicles, which run on mixtures of gasoline and up to 85% ethanol, are now available.

Ethanol production received a major boost with the passage of the Clean Air Act (CAA) Amendments of 1990. Provisions of the CAA established the Oxygenated Fuels Program and the Reformulated Gasoline Program in an attempt to control carbon monoxide and ground-level ozone problems. The desires to improve air quality and enhance energy security have encouraged an increased demand for ethanol.

The majority of ethanol produced in the U.S. is produced from starch obtained from maize (maize) grain. It is anticipated that current starch supplies will be insufficient to meet future demands for fermentable sugars. Ligno-cellulosic biomass, such as stover, can be used as an alternative source of fermentable sugars for the production of ethanol.

Stover consists of all parts (leaves, stalks; with the exception of kernels) of plants such as maize, sorghum, soybean, sugarcane, or other plants that are left in the field after the harvest. This stover biomass is rich in cellulose and hemicellulose, which are cell-wall polysaccharides that can release fermentable sugars upon treatment with enzymes (such as cellulases). The biomass conversion of maize stover is currently not very cost-effective.

One strategy to improve the overall efficiency of converting stover biomass to ethanol is to modify the chemical composition of maize stover, specifically the plant cell wall polymer lignin. Lignin has been shown to shield the cellulose, resulting in reduced access by cellulases. In addition, lignin has been shown to be an inhibitor of cellulases.

Brown midrib (bm) mutants of maize, easily identified by the reddish-brown color of their central leaf vein, have been known for more than 75 years. Similar mutants have been found in sorghum, sudangrass, and pearl millet (Barriere and Argillier, 1993, *Agronomie* 13: 865-876). These mutants have generated significant agronomic interest because their tissues are more easily digested by ruminants, providing better nutrition for livestock (Cherney et al., 1991, *Adv. Agron.* 46: 157-198). However, the known varieties of these plants are not widely grown as they often suffer from slow growth, increased susceptibility to pests, and an increased tendency to lodge, all of which lead to decreased yields.

The maize brown midrib mutations, specifically the bm1 mutation, result in the production of abnormal lignin (Kuc and Nelson, 1964, *Arch. Biochem. Biophys.* 105: 103-113). Four independent maize bm mutants are known, each affecting the lignin biosynthetic pathway. Bm1 mutants have reduced expression of cinnamyl alcohol dehydrogenase (CAD) activity (Halpin et al., 1998, *Plant J.* 14: 545-553). The CAD enzyme converts cinnamyl aldehydes to their alcohol derivatives in the last step of monolignol synthesis. The reduction of CAD activity in maize bm1 mutants leads to large increases in the hydroxycinnamylaldehyde content of the lignin (Provan et al., 1997, *J. Sci. Food Agric.* 73: 133-142), and such aldehydes have been implicated in formation of the red chromophore responsible, in part, for the defining coloration of the mutants (Higuchi et al., 1994, *J. Biotechnol.* 37: 151-158).

Two independent mutations have been identified in the O-methyltransferase (OMT) gene of bm3 maize (Vignols et al., 1995, *Plant Cell* 7: 407-416). The bm3 gene encodes caffeic acid O-methyltransferase, or more accurately named, a 5-hydroxyconiferaldehyde/5-hydroxyconiferyl alcohol O-methyltransferase (Humphreys et al., 1999, *Proc Natl Acad Sci USA* 96: 10045-10050). This enzyme catalyzes the methylation of the 5-position hydroxyl group of 5-hydroxyconiferyl aldehyde and 5-hydroxyconiferyl alcohol in monolignol synthesis. The net result of the bm3 mutation is a reduction in both the total amount of lignin deposited in the cell wall and a shift in lignin composition away from syringyl-type lignin because conversion of 5-hydroxyconiferyl aldehyde and 5-hydroxyconiferyl alcohol to sinapyl aldehyde and sinapyl alcohol, respectively is required for syringyl lignin synthesis. In bm3 mutants, the lignin also contains increased amounts of 5-hydroxyguaiacyl units, but in addition has a greatly reduced ratio of syringyl to guaiacyl units, as well as decreases in p-coumaric acid esters and overall lignin content (Chabbert et al., 1994, *J. Sci. Food. Agric.* 64: 349-355).

To improve the efficiency of converting biomass to ethanol, it would be advantageous to increase the amount of fermentable sugars in a plant stover. This invention provides that and related needs.

SUMMARY

The following embodiments and aspects thereof are described in conjunction with systems, tools and methods which are meant to be exemplary and illustrative, and not limiting in scope. In various embodiments, one or more of the above-described problems have been reduced or eliminated, while other embodiments are directed to other improvements.

A method of increasing yield of fermentable sugars in a plant stover is provided. The method may include the steps of producing a plant stover from a plant comprising a homozygous bm1 mutation and a homozygous bm3 mutation, and treating plant stover cell walls with a cellulolytic enzyme to produce a fermentable sugar.

A method of increasing yield of fermentable sugars in a plant stover is provided. The method may include the steps of producing a plant stover from a plant comprising a mutation in a gene that results in a reduction in cinnamyl alcohol dehydrogenase activity and further comprising a mutation in a gene that results in a reduction in O-methyltransferase activity, and treating plant stover cell walls with a cellulolytic enzyme to produce a fermentable sugar.

DETAILED DESCRIPTION OF THE INVENTION

Figure 1:
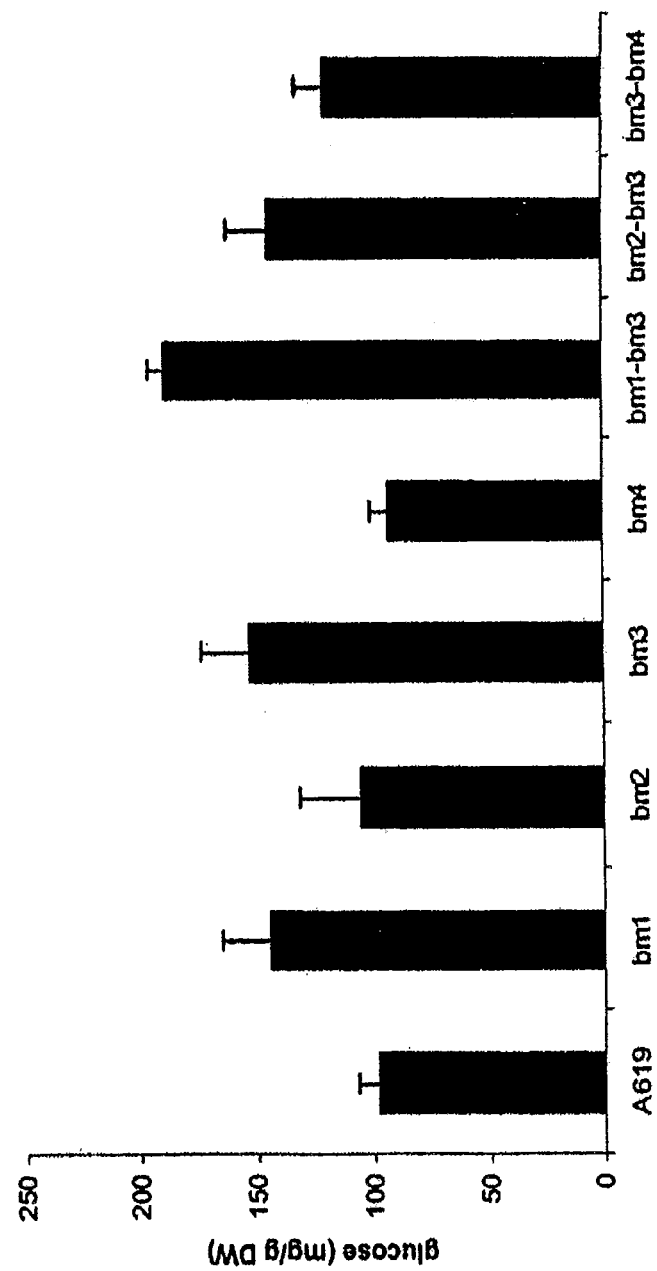
FIG. 1 depicts a graph showing glucose yields obtained from enzymatic saccharification of unpretreated maize stover from single and double bm mutants, compared to inbred lines A619 (wild-type control).

The following detailed description and examples are provided to further illustrate the present invention and are not intended to limit the invention beyond the limitations set forth in the appended claims.

Definitions

"Cellulolytic enzymes" include cellulose-degrading enzymes that include cellulases, cellobiohydrolases, cellobioses, and other enzymes involved in breaking down cellulose and hemicellulose into simple sugars such as glucose and xylose. Explicitly, but not exclusively, included within the term cellulose-degrading enzymes are those enzymes that fall under the Enzyme Classification heading EC 3.2.1.x. Preferably, "cellulolytic enzyme" means any enzyme or enzyme preparation exhibiting one or more of the following cellulolytic activities: endo-1,4-β-D-glucanase, exo-1,4-β-D-glucosidase, or β-D-glucosidase, which activities may be present to different extents in different preparations.

"Cell wall softener" means any physical, chemical, and/or biological methods that render the cellulose and hemicellulose content of the cell walls of the stover more accessible to enzymatic action. Examples of such methods include treatment of the stover with water or steam, concentrated or dilute acid or alkali, milling, etc.

"Plant" means any plant species, including, but not limited to, monocots and dicots. Examples of plants that can be used for practicing the invention include switch grass, maize, soybean, wheat, rice, alfalfa, potato, sugar beet, barley, millet, sunflower, sorghum, canola, rice, sorghum-sudan grass, pearl millet, and sugarcane.

"Near-isogenic mutants" means a group of mutants that are genetically identical except at one or a few loci. For example, near-isogenic maize bm mutants means maize lines that have a brown midrib (bm) mutation. These maize bm mutants can be single, double, triple, or more, depending on the number of mutations in comparison to the respective brown midrib allele from the wild-type maize control (A619).

"Stover" means all above-ground plant parts excluding the seed kernel.

"Fermentable sugars" means sugars that may be converted to ethanol. Glucose is an exemplary six carbon fermentable sugar derived from cellulose. Xylose is an exemplary five carbon fermentable sugar that is derived form hemicellulose.

Overview

The present invention provides a method of increasing yield of fermentable sugars in a plant stover. In one example, the method includes producing a plant stover from a plant comprising a homozygous bm1 mutation and a homozygous bm3 mutation. The produced plant stover is then treated with a cellulolytic enzyme to produce a fermentable sugar or sugars. In this example, the plant stover is obtained from a maize plant.

In another example, a method of increasing yield of fermentable sugars in a plant stover includes producing a plant stover from a plant that includes a mutation in a gene that results in a reduction in cinnamyl alcohol dehydrogenase activity, and also includes a mutation in a gene that results in a reduction in 5-hydroxyconiferaldehyde/5-hydroxyconiferyl alcohol O-methyltransferase activity. The produced plant stover is then treated with a cellulolytic enzyme to produce a fermentable sugar or sugars. In this example, the plant may be maize plant.

In another example, a method of increasing yield of fermentable sugars in a plant stover includes producing a plant stover from a plant that includes a down-regulated gene or gene product that results in a reduction in cinnamyl alcohol dehydrogenase activity, and also includes a down-regulated gene or gene product that results in a reduction in 5-hydroxyconiferaldehyde/5-hydroxyconiferyl alcohol O-methyltransferase activity. The produced plant stover is then treated with a cellulolytic enzyme to produce a fermentable sugar or sugars. In this example, the plant may be maize plant.

A variety of ways for down-regulation of cinnamyl alcohol dehydrogenase and 5-hydroxyconiferaldehyde/5-hydroxyconiferyl alcohol O-methyltransferase may be used. In one example, mutations in cinnamyl alcohol dehydrogenase and 5-hydroxyconiferaldehyde/5-hydroxyconiferyl alcohol O-methyltransferase may be used. For example, the mutations in cinnamyl alcohol dehydrogenase and 5-hydroxyconiferaldehyde/5-hydroxyconiferyl alcohol O-methyltransferase may be transcriptional, translational, post-translational, or may include any combinations thereof.

Furthermore, down-regulation of cinnamyl alcohol dehydrogenase and 5-hydroxyconiferaldehyde/5-hydroxyconiferyl alcohol O-methyltransferase may be induced by various genetic engineering means known in the art, for example transgenes, sense RNA, antisense RNA, RNAi, transcriptional factors, transgenic plants, combinations of the above, etc. The down-regulation may be transcriptional, translational, post-translational, or may include any combinations thereof. Thus, both the genes and/or the respective gene products may be genetically modified. Similarly, down-regulation of one of the genes (e.g. cinnamyl alcohol dehydrogenase)

may be caused by a mutation, whereas the other gene (e.g. 5-hydroxyconiferaldehyde/5-hydroxyconiferyl alcohol O-methyltransferase) may be down-regulated by antisense RNA or in some other way. The particular mechanisms of the down-regulation of cinnamyl alcohol dehydrogenase and 5-hydroxyconiferaldehyde/5-hydroxyconiferyl alcohol O-methyltransferase are not important, so long as the down-regulations result in decreased activity of both cinnamyl alcohol dehydrogenase and 5-hydroxyconiferaldehyde/5-hydroxyconiferyl alcohol O-methyltransferase, and those decreases result in an increased yield of fermentable sugars as compared to wild-type plants where bm1 and bm3 are not down-regulated.

A variety of cellulolytic enzymes also may be used. A nonlimiting list of cellulose-degrading enzymes includes those enzymes that fall under the Enzyme Classification heading EC 3.2.1.x. Preferably, "cellulolytic enzyme" means any enzyme or enzyme preparation exhibiting one or more of the following cellulolytic activities: endo-1,4-β-D-glucanase, exo-1,4-β-D-glucosidase, or β-D-glucosidase, which activities may be present to different extents in different preparations. The activity of cellulolytic enzymes can be assayed using methods known in the art, e.g., cellulose assays described in U.S. Pat. No. 6,818,803, herein incorporated by reference. Some of these methods are also described in the Examples section below.

After the production of plant stover as indicated above, and prior to treatment of the stover with a cellulolytic enzyme, the stover may be treated with a cell wall softener. This can be accomplished by any means known in the art, e.g. any physical, chemical, and/or biological methods that render the cellulose and hemicellulose content of the cell walls of the stover more accessible to enzymatic action. Examples of such methods include treatment of the stover with water or steam, concentrated or dilute acid or alkali, milling, etc.

EXAMPLES

The invention will be further described by reference to the following detailed examples. These examples are provided for purposes of illustration only, and are not intended to limit the claimed invention.

Example 1

Production of Bm1-Bm3 Double Mutant Maize Plants

Double bm1-bm3 mutant maize plants were produced by crossing an A619 inbred maize plant containing the bm3 mutation with an A619 inbred maize plant containing the bm1 mutation. Since both these mutations are recessive the $F_2$ progeny did not display a mutant phenotype because they were heterozygous at both loci. The $F_1$ progeny were self-pollinated and $F_2$ progeny that were homozygous for both mutations were selected. The $F_2$ progeny that were homozygous for both mutations were self-pollinated to further produce homozygous bm1-bm3 double mutant plants.

The bm1 mutation was first described by Eyster, 1926, *Science* 64: 22. Seed containing the bm1 mutation is available from the Maize Genetics COOP Stock Center at the University of Illinois in Urbana-Champaign, Ill. (http://w3.ag.uiuc.edu/maize-coop/mgc-info.html). The bm3 mutation was first mentioned by Emerson et al., 1935, *Maize Ill Univ. Agric. Exp. Stn. Memoir* 180: 1-83. Seed containing the bm3 mutation was obtained from the Maize Genetics COOP Stock Center. The A619 inbred line is a public inbred line and can be obtained through public germplasm collections, such as the National Plant Germplasm System (http://www.ars-grin.gov/npgs/).

Example 2

Enzymatic Hydrolysis of Bm1-Bm3 Double Mutants

The bm1-bm3 double mutant maize plants were evaluated for biomass conversion properties in a lab-scale setting. The standard National Renewable Energy Lab procedure for enzymatic hydrolysis of stover with a mix of cellulolytic enzymes was used (Brown and Torget, 1996, Enzymatic Saccharification of Lignocellulosic Biomass, LAP-009, NREL Ethanol Project). The hydrolysis was performed on 300 mg of unpretreated stover using six filter paper units (FPU) of a commercial cellulase cocktail consisting of a 1:1 (v/v) mix of NOVOZYME 188 and CELLUCLAST 1.5 L in 50 mM citrate buffer (pH 4.8). Hydrolysis was performed at 50° C. for 24 hours; the mixture was shaken during hydrolysis. The concentration of glucose produced by this process was measured with an ACCU-CHEK ADVANTAGE blood glucose meter that had been calibrated using a set of standard glucose solutions in the hydrolysis buffer. FIG. 1 shows the yield of glucose from the 2004 stover samples.

FIG. 1 shows glucose yields obtained from enzymatic saccharification of unpretreated maize stover from single and double bm mutants (Summer 2004 harvest), compared to inbred lines A619 (wild-type control). The hydrolysis was performed on 300 mg stover (not pretreated), using 6 FPU (filter paper units) of a commercial cellulase cocktail consisting of a 1:1 (v/v) mix of Novozyme 188 and Celluclast 1.5 L in 50 mM citrate buffer (pH 4.8). Hydrolysis was performed at 50° C. for 24 hours, while shaking. The glucose concentration was measured with an Accu-Chek® Advantage® blood glucose meter that had been calibrated using a set of standard glucose solution in the hydrolysis buffer. The yield of glucose per gram dry weight is displayed along the vertical axis.

The data in FIG. 1 show that the bm1 and bm3 mutations result in higher yields of glucose while the bm2 and bm4 mutations result in glucose yields that are not significantly different from the wild type. Likewise the bm2-bm3 and bm3-bm4 double mutants did not perform better than the bm3 single mutant, although compared to the bm2 and bm4 single mutants, the yield of these double mutants did benefit from the introduction of the bm3 mutation. The bm9-bm3 double mutant was the best performer in terms of its glucose yield with on average 2.3 times as much glucose as the wild-type control per gram dry weight under the stated assay conditions.

Combining bm1 and bm3 resulted in substantial improvement in glucose yield. This improvement occurred without pre-treatment of the stover and resulted in glucose yields typically obtained from wild-type stover after pre-treatment. Thus, the combination of the bm1 and bm3 mutations can provide significant cost savings when biomass conversion occurs on a large scale.

Example 3

Variation in Enzyme Hydrolysis Rate

The higher yield of glucose obtained from the stover of some of the mutants (FIG. 1) can be the result of (1) an increased rate of hydrolysis, (2) an overall higher yield of glucose, or (3) the combination of (1) and (2). To investigate this, a 168-hour hydrolysis experiment was performed, during which hydrolysate samples were collected at 0, 24, 48, 75 and 168 hours. This experiment was performed on wild-type, bm3 and bm1-bm3 stover (three replicate samples of each genotype). In addition to the hydrolysis, the cellulose content of all samples was determined.

Figure 2:
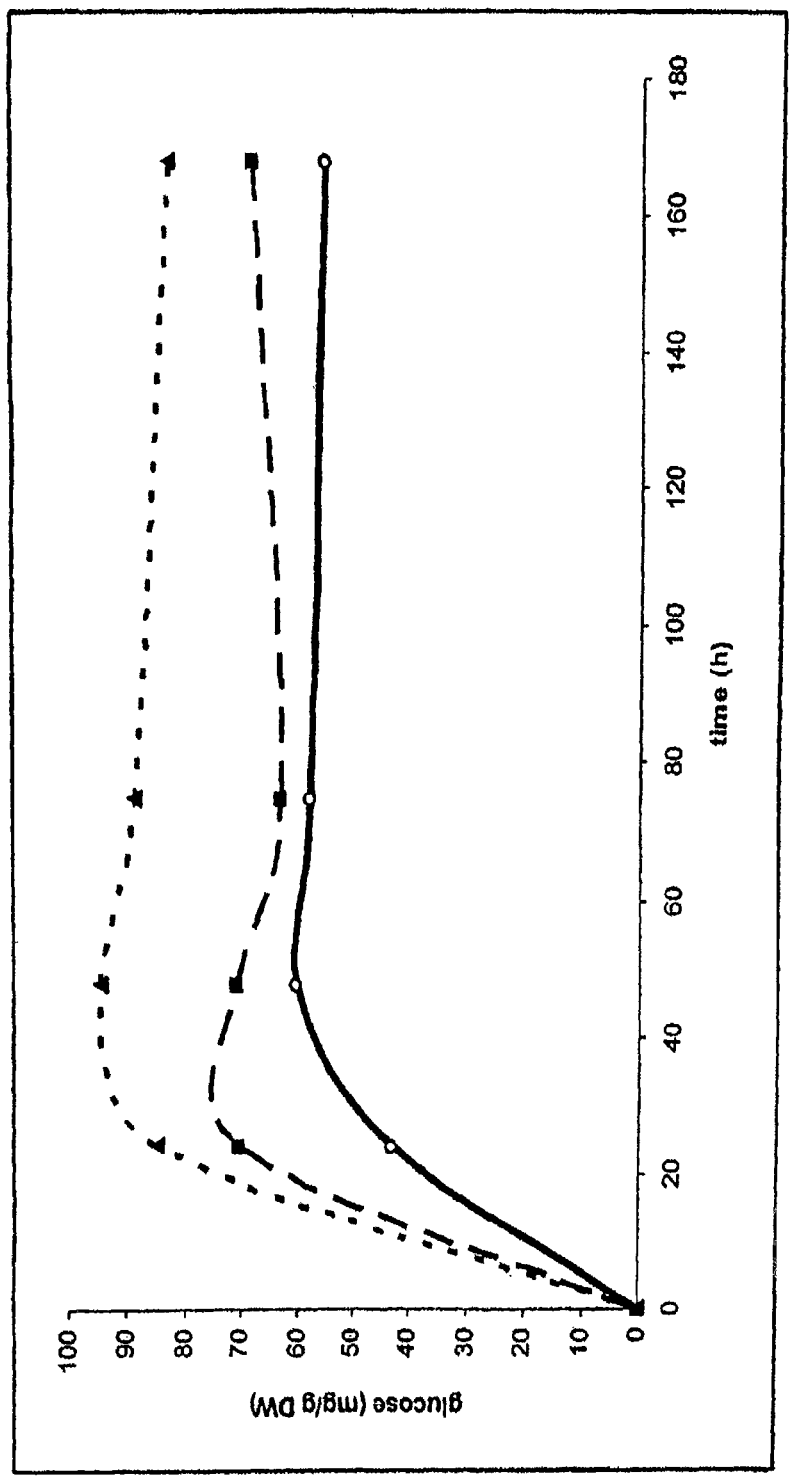
FIG. 2 depicts: A, a graph showing the average rate of hydrolysis of stover from wild type (♦), bm3 (■), and bm1-bm3 (▲); B, the relative cellulose content of the stover obtained from wild type (A619), bm3, and bm1-bm3 mutant plants.
Figure 2B:
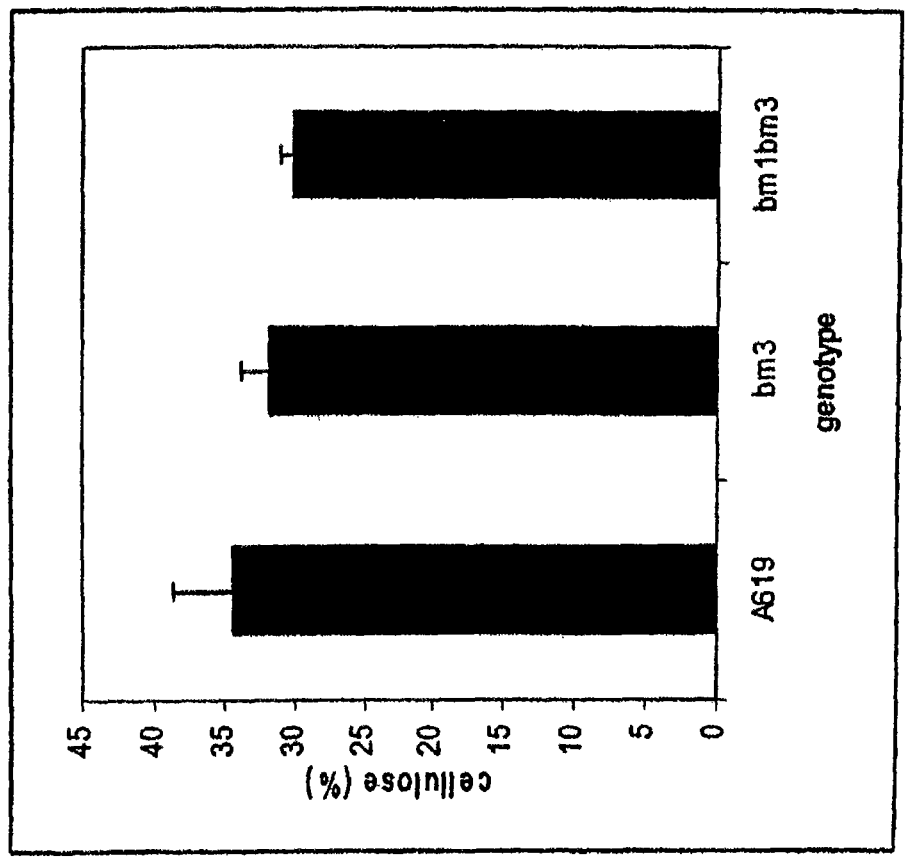

The results from this analysis are depicted in FIG. 2. FIG. 2A shows the average rate of hydrolysis of stover from wild type (A619), bm3 and bm1-bm3 mutant plants. The concentration of glucose was measured with the Precision QID blood glucose meter which is specific for glucose. FIG. 2B shows the cellulose content of the stover obtained from wild type (A619), bm3 and bm1-bm3 mutant plants.

Based on a t-test, the variation in cellulose content between the three different genotypes was not statistically significant. For the wild-type, bm3, and bm1-bm3 stover, 20, 25 and 32%, respectively, of the cellulose was converted to glucose, expressed on the basis of the dry weight of stover (i.e. 100 mg glucose/g dry weight obtained from stover containing 300 mg cellulose/gram dry weight constitutes a 33% conversion). Based on these data the observed differences between genotypes in the rate and yield of hydrolysis between the three genotypes are therefore best explained by scenario (3): higher rate of hydrolysis and higher overall yield of glucose.

Example 4

Stover Pre-Treatment

The composition of the biomass as described in this invention, impacts the severity of processing that must be carried out in the first two steps and thereby directly impacts processing costs. Stover was selected from the wild-type control and the mutants bm2 and bm3 for pretreatment experiments in which the experimental conditions were varied. The three main processing parameters for acid catalyzed pretreatments were: pH, reaction temperature, and reaction time. These three factors were combined into a single number representing the severity of the pretreatment. The combined severity factor (CSF), shown in Equation 1, fairly accurately models the improvement to digestibility from pretreatment by a single number. In batch, dilute sulfuric acid pretreatment of maize stover, Yang and Wyman (2004) have shown that maize stover pretreated to the same "combined severity factor" exhibit similar digestibility for most combinations of pH, time, and temperature having a constant combined severity factor.

Equation 1:

$$CSF = \log R_o - pH \quad (1)$$

where
$R_o = t \times e^{(T-100)/14.75}$
t=reaction time, min
T=reaction temperature, ° C.

Figure 3:
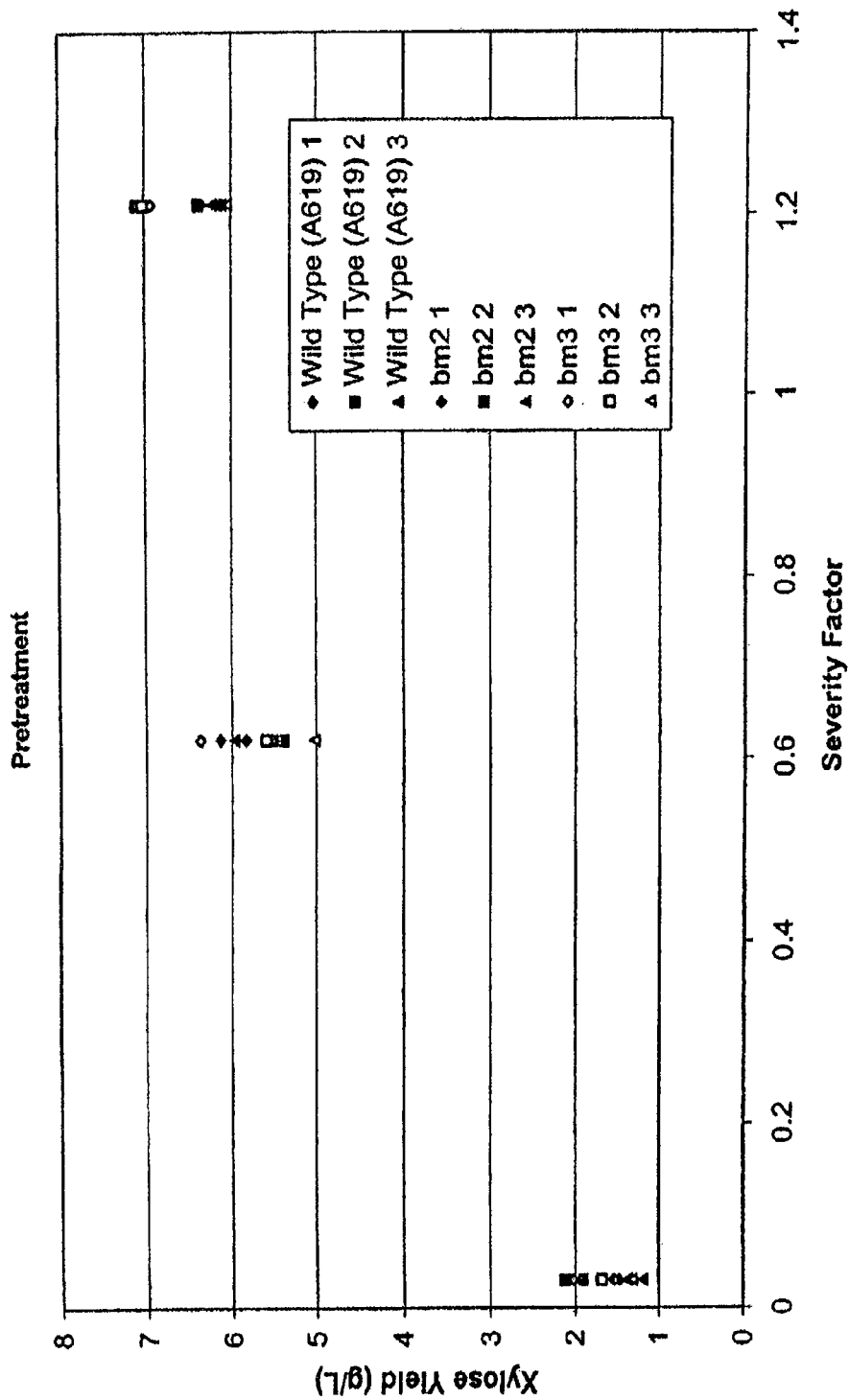
FIG. 3 depicts a graph showing xylose yields from the pretreatment of maize wild-type, bm2, and bm3 mutant stover.

For the results shown in FIG. 3, three different combined severity factors were examined (0.03, 0.62, 1.21) which correspond to three different temperatures (130° C., 150° C. and 170° C.) of 50 mM sulfuric acid for a reaction time of 5 minutes each. These severity factors represent mild to moderate pretreatment conditions that are in the range of optimal pretreatment conditions. Maize stover samples were ground to pass a 40 mesh screen and then were loaded into modified borosilicate vials and sealed. Each reactor contained a total volume of 1.5 mL. The stover was loaded into the reactor at the equivalent of 3% by total slurry mass.

These hydrolysis experiments were used to study the interactions between cell wall composition and the release of monosaccharides during pretreatment. The effect of dilute acid and liquid hot water pretreatments is largely to solubilize the hemicellulose fraction of the plant cell wall, thus opening the structure to improved access by the cellulolytic enzymes.

FIG. 3 depicts a graph showing xylose yields from the pretreatment of maize wild-type, bm2, and bm3 mutant stover. Samples from three individual plants of each type were pretreated in duplicate. As shown in FIG. 3, the data from these experiments indicated that the mutants behaved similarly in the hydrolysis process to the wild-type control. The brown midrib mutations did not positively or negatively affect the acid catalyzed hydrolysis of the hemicellulose. These results indicate that brown midrib stover performed similarly to wild type stover in acid catalyzed pretreatments (including liquid hot water pretreatment) with respect to the thermochemical reactions of hemicellulose hydrolysis.

Pretreatment may be carried out to minimize hydrolysis, and to "soften" the lignocellulose by pressure—cooking it in water to dissolve most of the hemicellulose and some of the cellulose into water soluble oligosaccharides. The lignin structure may affect this step—since a change in lignin structure could modify the covalent linkage of the hemicellulose to the lignin, with more labile bonds between the two being more readily broken in water at a pH maintained at pH 4 to 7 and a temperature of 140 to 200° C., thereby releasing oligosaccharides at conditions encountered in a biomass to ethanol pretreatment process. The lignin-hemicellulose bonds will still be sufficiently stable to confer protective effects and physical stability in the field where temperatures do not exceed 45° C.

Example 5

Pyrolysis-Gas Chromatograms of Stover

Figure 4:
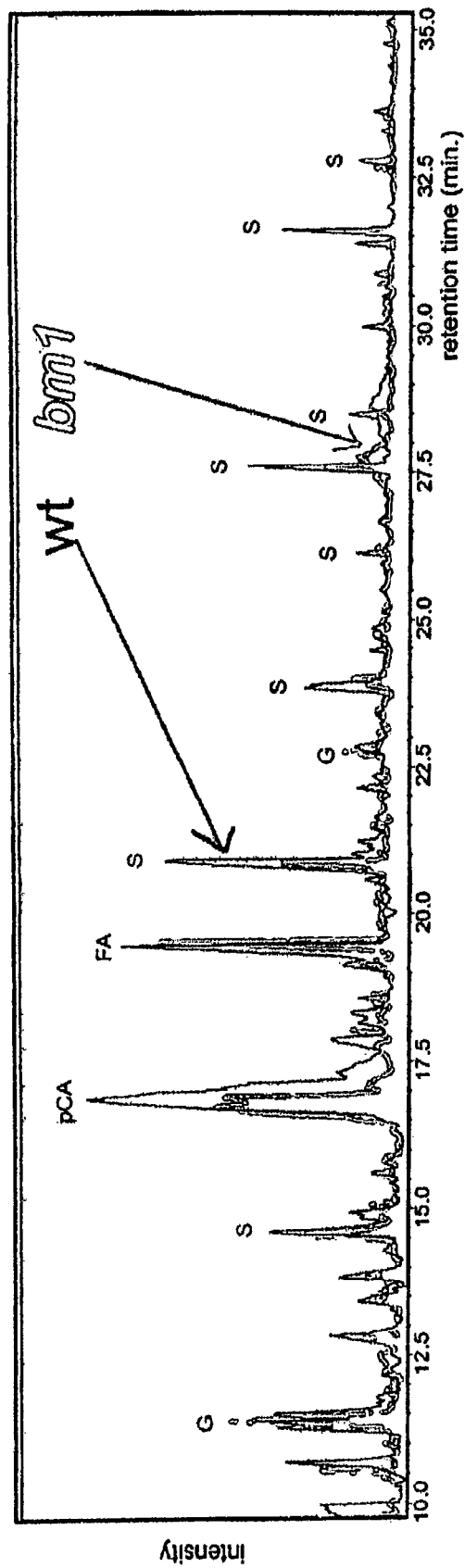
FIG. 4 depicts graphs showing pyrolysis-gas chromatograms of stover obtained from: A, wild-type (wt) maize inbred A619 (black) and a near-isogenic bm1 mutant (teal); B, wild-type maize inbred A619 (black) and a near-isogenic bm3 mutant (red); C, the near-isogenic bm3 (red) and bm1-bm3 (blue) mutants.
Figure 4:
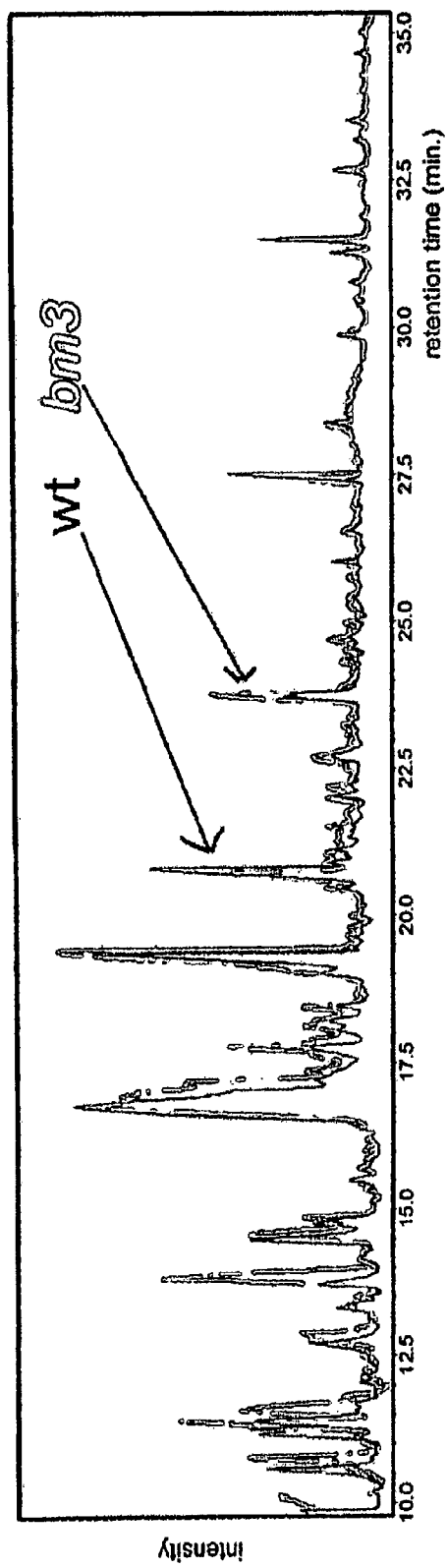
Figure 4:
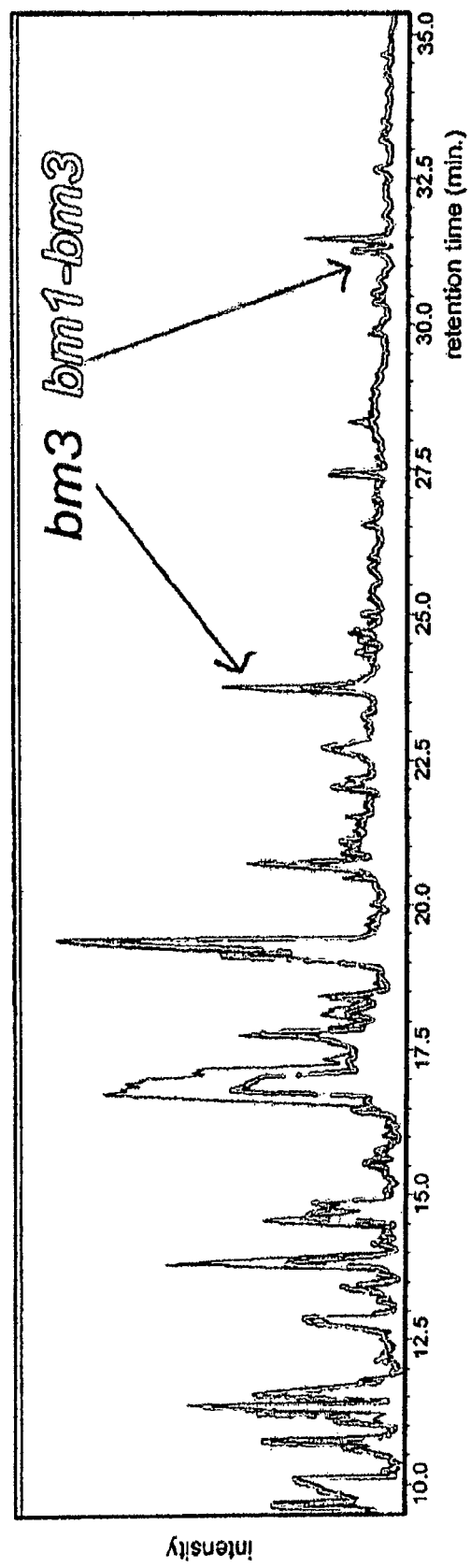

Further analyses of the changes in the biochemical composition of the bm1-bm3 double mutant were conducted using gas chromatography. FIG. 4 shows pyrolysis-gas chromatograms of stover obtained from: A, wild-type (wt) maize inbred A619 (black) and a near-isogenic bm1 mutant (teal); B, wild-type maize inbred A619 (black) and a near-isogenic bm3 mutant (red); and C, the near-isogenic bm3 (red) and bm1-bm3 (blue) mutants.

The origin of several peaks in FIG. 4 is labeled as follows: G and S refer to compounds in the pyrolysate derived from guaiacyl and syringyl residues in the lignin, respectively. Further, pCA and FA refer to compounds derived from p-coumaric acid and ferulic acid, respectively. Note the similarity in the changes in composition in the bm1 and bm3 stover relative to the wild-type control, specifically the reduction in the peak heights of S- and pCA-derived compounds. The composition of the stover from the bm1-bm3 double mutant shows an even further reduction in these compounds, as is evident from panel C. These chemical changes are consistent with the observation that an increase in the G:S ratio in the lignin enhances the yield of fermentable sugars that is obtained from enzymatic saccharification.

While a number of exemplary aspects and embodiments have been discussed above, those of skill in the art will recognize certain modifications, permutations, additions and sub-combinations thereof. It is to be understood that this invention is not limited to the particular methodology, protocols, patients, or reagents described, and as such may vary. It is also to be understood that the terminology used herein is for the purpose of describing particular embodiments only, and is not intended to limit the scope of the present invention, which is limited only by the claims.

We claim:

1. A method of increasing yield of fermentable sugars in a plant stover, the method comprising: producing a plant stover from a plant comprising a homozygous bm1 mutation and a homozygous bm3 mutation; and, treating the plant stover with a cellulolytic enzyme to produce a fermentable sugar.

2. The method of claim 1, further comprising treating the plant stover with a cell wall softener to soften plant stover cell walls before treating the plant stover with a cellulolytic enzyme.

3. The method of claim 1, where the plant stover is produced by growing plants from seed and harvesting the plants.

4. The method of claim 3, where the cell wall softener is selected from the group consisting of sulfuric acid and hot water.

5. The method of claim 1, where the plant is selected from the group consisting of switch grass, maize, soybean, wheat, rice, alfalfa, potato, sugar beet, barley, millet, sunflower, sorghum, canola, rice, sorghum-sudan grass, pearl millet, and sugarcane.

6. The method of claim 5, where the plant is maize.

7. The method of claim 1, where the fermentable sugar is selected from the group consisting of xylose and glucose.

8. A method of increasing yield of fermentable sugars in a plant stover, comprising: producing a plant stover from a plant comprising a mutation in a first gene that results in a reduction in cinnamyl alcohol dehydrogenase activity and further comprising a mutation in a second gene that results in a reduction in 5-hydroxyconiferaldehyde/5-hydroxyconiferyl alcohol O-methyltransferase activity; and
treating the plant stover with a cellulolytic enzyme to produce a fermentable sugar.

9. The method of claim 8, further comprising the step of treating the plant stover with a cell wall softener to soften plant stover cell walls before treating the plant stover cell walls with a cellulolytic enzyme.

10. The method of claim 8, where the plant stover is produced by growing plants from seed and harvesting the plants.

11. The method of claim 8, where the cell wall softener is selected from the group consisting of sulfuric acid and hot water.

12. The method of claim 8, where the plant is selected from the group consisting of switch grass, maize, soybean, wheat, rice, alfalfa, potato, sugar beet, barley, millet, sunflower, sorghum, canola, rice, sorghum-sudan grass, pearl millet, and sugarcane.

13. The method of claim 12, where the plant is maize.

14. The method of claim 8, where the fermentable sugar is selected from the group consisting of xylose and glucose.

15. A method of increasing the yield of fermentable sugars in a plant stover, comprising: producing a plant stover from a transgenic plant with a reduced cinnamyl alcohol dehydrogenase activity and reduced 5-hydroxyconiferaldehyde/5-hydroxyconiferyl alcohol O-methyltransferase activity in comparison with a wild-type plant grown under substantially similar conditions; and treating the plant stover with a cellulolytic enzyme to produce a fermentable sugar.

16. The method of claim 15, further comprising the step of treating the plant stover with a cell wall softener to soften plant stover cell walls before treating the plant stover cell walls with a cellulolytic enzyme.

17. The method of claim 15, where the plant stover is produced by growing plants from seed and harvesting the plants.

18. The method of claim 15, where the cell wall softener is selected from the group consisting of sulfuric acid and hot water.

19. The method of claim 15, where the plant is selected from the group consisting of switch grass, maize, soybean, wheat, rice, alfalfa, potato, sugar beet, barley, millet, sunflower, sorghum, canola, rice, sorghum-sudan grass, pearl millet, and sugarcane.

20. The method of claim 19, where the plant is maize.

21. The method of claim 15, where the fermentable sugar is selected from the group consisting of xylose and glucose.

* * * * *